US00PP26343P2

(12) United States Plant Patent
Hansen

(10) Patent No.: US PP26,343 P2
(45) Date of Patent: Jan. 19, 2016

(54) *SALVIA* PLANT NAMED 'PINK DAWN'

(50) Latin Name: ***Salvia* hybrid**
Varietal Denomination: Pink Dawn

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 141 days.

(21) Appl. No.: 13/999,909

(22) Filed: Apr. 2, 2014

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para

(57) ABSTRACT

The new and distinct cultivar of perennial *Salvia* plant named 'Pink Dawn' characterized by its large cotton candy-colored flowers densely arranged in verticils. The new plant has a compact habit with stiff, upright, heavily-branched stems showing strong greyed-purple tinting and persistent calyxes of similar greyed-purple tinting, a strong vigorous growth rate and gray-green foliage.

1 Drawing Sheet

Botanical denomination: *Salvia* hybrid.
Cultivar designation: 'Pink Dawn'.

BACKGROUND OF THE INVENTION

The present invention relates to a new and distinct cultivar of ornamental Sage plant hereinafter referred to by the cultivar name *Salvia* 'Pink Dawn' or as the new plant. The new plant was discovered as a random seedling by the inventor in the summer of 2011 in a residential garden planting in Zeeland, Mich., USA. The nearest *Salvia* planted in the area was *Salvia* 'May Night'. The new plant was an isolated whole plant of flowering size. The new *Salvia* was further evaluated and asexually propagated by basal cuttings taken by the inventor in Zeeland, Mich., USA in 2012. *Salvia* 'Pink Dawn' was then further evaluated and the resulting asexually propagated plants of the new plant have been found to be true to type and stable in successive generations.

SUMMARY OF THE INVENTION

Plants of *Salvia* 'Pink Dawn' have not been observed under all possible environmental conditions. The phenotype may vary somewhat with variations in environment such as temperature, nutrition and light intensity without, however, any variance in genotype.

*Salvia* 'Pink Dawn' can be most closely compared to *Salvia* 'Sweet 16' U.S. Plant Pat. No. 24,312. Compared to 'Sweet 16', the new plant flowers about a week longer because of the greater branching of *Salvia* 'Pink Dawn', and the new plant also has much darker greyed-purple flower stems and darker green basal foliage. The new plant can also be compared to *Salvia* 'Endless Love' U.S. Plant Pat. No. 21,707 which has a *Salvia verticillata* background and flowers on whorled scapes that are more purple less pink and smaller in size, and 'Pink Dawn' has darker greyed-purple flower stems.

*Salvia* 'Pink Dawn' can also be compared to *Salvia* 'Pink Delight' U.S. Plant Pat. No. 14,965, *Salvia* 'Sensation Deep Rose Improved' (U.S. Plant Patent pending by another inventor) and *Salvia* 'New Dimension Rose' (not patented). In comparison to 'Pink Delight' and *Salvia* 'Eveline', *Salvia* 'Pink Dawn' has lighter pink flowers. *Salvia* 'Eveline' is also taller and *Salvia* 'New Dimension Rose' is shorter than *Salvia* 'Pink Dawn'. *Salvia* 'Endless Love' U.S. Plant Pat. No. 21,707 is from the species verticillata and greater separation of the verticils nodes and smaller and more purple flowers. The stems and calyxes of 'Pink Dawn' are much darker pigmented with greyed-purple than all of the above comparison plants.

The following characteristics in combination distinguish *Saliva* 'Pink Dawn' as a new and distinct cultivar from all other cultivars known to the inventor:

1. Very large cotton candy-pink flowers densely arranged in verticils;
2. Stiff, upright, heavily-branched stems with heavy dark greyed-purple tinting;
3. Fuchsia-colored flower buds and persistent dark greyed-purple calyxes;
4. Compact, rounded, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Pink Dawn'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed. Plant growth regulators have been used in greenhouse grown trials only.

DETAILED BOTANICAL DESCRIPTION

Figure 1:
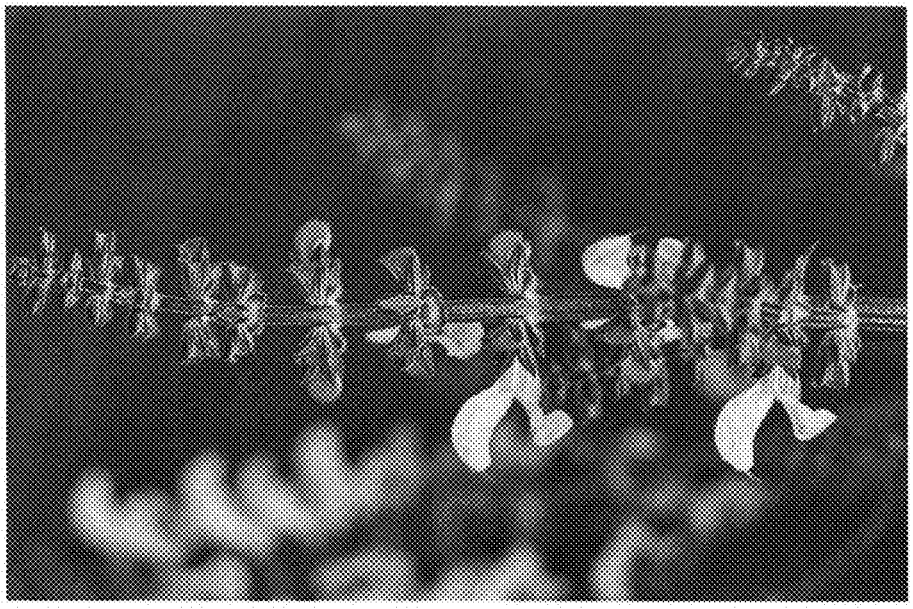
FIG. 1 shows a close-up of the flower scape with the buds, pink flowers and dark stems and calyxes.
Figure 2:
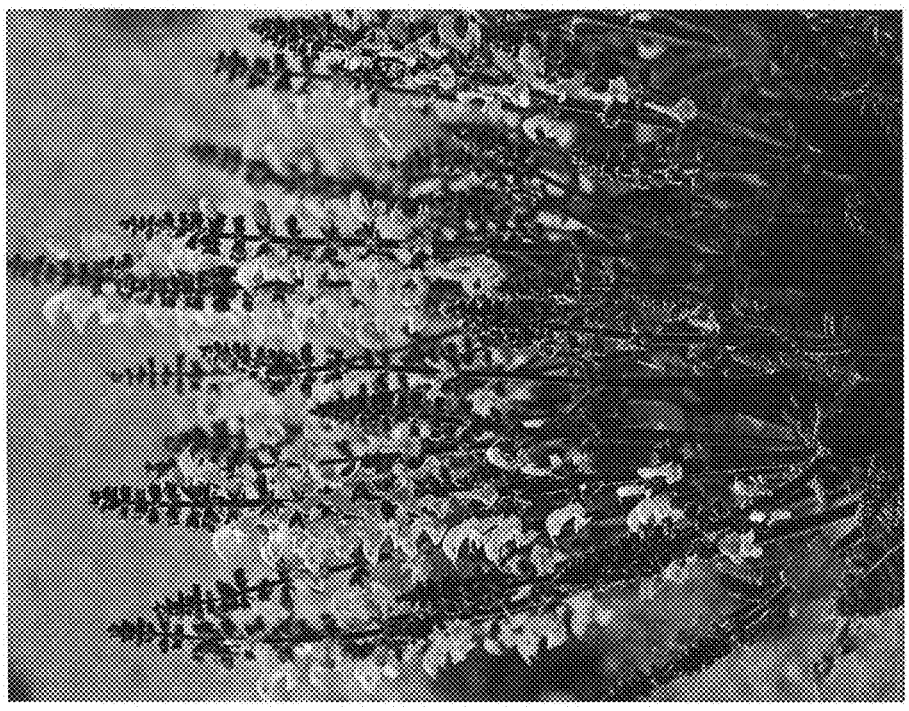
FIG. 2 shows the plant habit in full flower in a landscape.

The following descriptions and color references except where common dictionary terms are used are based on the 2001 edition of The Royal Horticultural Society Colour Chart. *Salvia* 'Pink Dawn' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a wholesale perennial nursery in Zeeland, Mich. and greenhouse forced two-year old plants. Plants were given supplemental water and fertilizer and plant growth regulators were used for the greenhouse trials only.

Botanical classification: *Salvia pratense* (Linnaeus).

Parentage: Female or seed parent is unknown; unknown male or pollen parent.

Plant habit: Winter-hardy herbaceous perennial; multi-stemmed, compact, rounded, with mostly basal foliage, and flowers in several tightly arranged verticils on branched upright racemes displayed above foliage; in flower with panicles about 52 cm tall and about 52 cm wide at the fullest point; foliage extends up the stems about 25 cm tall and 42 cm wide at base.

Propagation: By herbaceous tip cuttings; time to produce a rooted stems about two weeks.

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color.

Foliage: Opposite, simple, rugose, lanceolate; margin crenate, glabrous upper and lower surfaces except veins; acute apex and base cordate to auriculate with lobes sometimes overlapping; lightly pubescent both surfaces; size to about 20.0 cm long; leaf blades about 12.0 cm long and 5.5 cm across, decreasing in size distally; average about 10.0 cm long and 3.0 cm across; faint sage fragrance.

Foliage color: Adaxial surface nearest RHS 137A; abaxial surface between RHS N138C and RHS 137C.

Venation: Reticulate; impressed on adaxial side and ridged on abaxial side; pubescent, more heavily on abaxial.

Vein color: Adaxial midrib and main veins between RHS 138D and RHS 139D, main veins and secondary veins gradually darkening to nearest RHS 137A; abaxial midrib between RHS 145D and RHS 139D, main and secondary veins gradually darkening to nearest RHS 137C toward leaf margin.

Petiole: Concave adaxial side, convex abaxial side, pubescent; to about 8.0 cm long and 5.0 mm wide, average 4.0 cm long and 3.5 mm wide at base.

Petiole color: Adaxial and abaxial surfaces between RHS 138B and RHS 138D and margins between RHS 139B and RHS 139C.

Flower description: Perfect, bilabiate, verticillate with flowering generally beginning at lower verticils and advancing up the scape, but not all flowers at each verticil opening at the same time giving the effect of a scape being in continuous flower for longer periods; average distance between verticils about 17.0 mm, greater proximally and less distally; with midline projected at about 90 degree angle to stem and banner petal about 10 degree angle above horizontal; self-cleaning, petals not persistent; flowering beginning late spring for about six weeks and repeating if initial scapes removed.

Flower longevity: About four days on the plant or as cut flower.

Fragrance: None detected under present growing conditions.

Flower buds one to two days prior to anthesis: Shape is rounded on top and slightly concave below, with rounded apex; pubescent; about 1.8 cm long, 8.0 mm tall and 3.0 mm wide.

Bud color: Petals between RHS N78A and RHS N78B; abaxial calyx distal region darker than RHS 187A and less gray than RHS N186B but more gray than RHS N186C, with less direct light base between RHS N138B and RHS 137B, with veins and portions of distal region in more light heavily tinted with nearest RHS N186B; adaxial calyx base nearest RHS 147D, and proximal region between RHS 147B and RHS 147C with darker veins of nearest RHS 137C.

Flowers: About 2.4 cm long, 2.0 cm tall and 5.0 mm wide; clustered at verticils with about six flowers per verticil.

Petals: Bilabiate corolla; upper banner petal and flattened side to side vertically, with notched apex and base fused with labium.

Banner (upper) petal: Minutely pubescent outside, glabrous inside; about 2.4 cm long, 1.0 cm tall and 0.5 cm across.

Labium (lower) petal: Consisting of four lobes, two proximal lobes about 3.0 mm long and 2.0 mm wide at base with acute apex, two distal lobes about 4.0 mm long 4.0 mm wide with a 1.0 mm apical notch between; lower labium slightly concaved upwards, about 1.2 cm long, 5.0 mm wide at the widest portion and 8.0 mm tall.

Petal color: Upper banner petal nearest RHS N78C inside and outside; lower labium petal between RHS N78C and RHS N78B in both inner and outer surfaces; fused base inside calyx near white, much lighter than RHS N155D.

Androecium: Two, fused with labium, contained within banner petal except when triggered by pollinator.

*Filament*.—Glabrous, fused about 6.0 mm from base of labium petal; curved around inside of banner petal; about 6.0 mm long and less than 0.5 mm diameter with a 1.0 mm trip mechanism at base; color of base whiter than RHS 155D, nearest RHS 77D at distal region before stamen.

*Anther*.—Glabrous, oblong, about 3.0 mm long and 1.0 mm diameter; longitudinal, dorsifixed; color nearest RHS N186C.

*Pollen*.—Globose, less than 0.5 mm circumference; color nearest RHS 17D.

Gynoecium: One, curved around inside of banner petal.

*Style*.—About 2.4 cm long and less than 1 mm diameter; color lighter than RHS 155D and darkening just before stigma split to nearest RHS N79B.

*Stigma*.—Split in two and curved in the terminal 2.0 mm; apex pointed; color nearest RHS N79B.

*Ovary*.—Superior; color more green than RHS 145A and more yellow than RHS 138B.

*Fruit*.—Nutlet, up to four at base inside calyx; rounded, about 1.5 mm diameter; color darker than RHS 200A.

Calyx: Five sepals, three upper and two lower, campanulate, apex acute; fused base; tube about 8.0 mm long and 5.0 mm tall at mouth and 3.0 mm wide; lower set fused to within 4.0 mm of apex and cleft about 3.0 mm deep between upper and lower set; upper set of three fused to closer than 1.0 mm of apex.

Calyx color: Abaxial bases and regions in little direct sunlight between RHS 138A and RHS 139C developing solid tinting of between RHS N187A and RHS N186B especially with more light; adaxial between RHS 137D and RHS 139C with darker veins of RHS 137B toward apex.

Bracts: Each verticil subtended by two opposite bracts; apex acuminate, base attenuate, shape nearly cordate; coarsely wavy to bent downward toward apex; margin minutely pubescent, and glabrous above and below; bract size up to 15.0 mm long and 10.0 mm wide, decreasing distally; color variable with light intensity, in less light abaxial and adaxial surfaces nearest RHS 141B on margin about 1.0 mm wide, with center and base vein nearest RHS 155A; color with more intense light between RHS N186C and RHS N186D on both surfaces throughout.

Peduncles: Quadrangular in cross section, about 16 per plant; strong; up to 52 cm tall and 5.0 mm across; finely pubescent; branches in lower two to four nodes, upright at 45 degrees from horizontal or greater, branches to about 25.0 cm long and 3.0 mm across; average internode distance about 5.0 cm.

Peduncle color: Between RHS 138A and RHS 138B and lower regions with heavy tinting in upper regions and portions with more intense light nearest RHS 187A to completely RHS 187A.

Pedicels: Cylindrical, about 2.0 mm long and 0.5 mm diameter; pubescent; horizontal to about 20 degrees above horizontal.

Pedicel color: Variable with light intensity, between RHS 146C and RHS 146D in regions with lower light and nearest RHS N187A in portions with intense light.

Disease and pest resistance: Plants of *Salvia* 'Pink Dawn' perform best with adequate moisture and good drainage and are hardy from USDA zone 3 to 8. Resistant to diseases and pests beyond that common to *Salvia* has not been noted.

It is claimed:

1. The new and distinct perennial *Salvia* plant named 'Pink Dawn' as herein described and illustrated useful for landscaping as a specimen plant, en masse or as a cut flower.

* * * * *